US008445462B2

(12) United States Patent
Escaich Ferrer et al.

(10) Patent No.: US 8,445,462 B2
(45) Date of Patent: May 21, 2013

(54) COMPOSITION FOR THE TREATMENT OF OSTEOARTHRITIS

(75) Inventors: Josep Escaich Ferrer, Barcelona (ES); Ana Maria Torrent Gibert, Barcelona (ES); Ramon Ruhi Roura, Barcelona (ES); Pere Dalmau Castanares, Barcelona (ES)

(73) Assignee: Bioiberica, S.A., Barcelona (ES)

( * ) Notice: Subject to any disclaimer, the term of this patent is extended or adjusted under 35 U.S.C. 154(b) by 218 days.

(21) Appl. No.: 12/810,775

(22) PCT Filed: Dec. 17, 2008

(86) PCT No.: PCT/EP2008/067683
§ 371 (c)(1),
(2), (4) Date: Jun. 25, 2010

(87) PCT Pub. No.: WO2009/083444
PCT Pub. Date: Jul. 9, 2009

(65) Prior Publication Data
US 2010/0286086 A1    Nov. 11, 2010

(30) Foreign Application Priority Data
Dec. 28, 2007  (ES) .................................. 200703459

(51) Int. Cl.
*A61K 31/715* (2006.01)
*A61K 31/737* (2006.01)
*A61P 19/02* (2006.01)
*A61P 29/00* (2006.01)

(52) U.S. Cl.
USPC ........................................................ 514/54

(58) Field of Classification Search
USPC ........................................................ 514/54
See application file for complete search history.

(56) References Cited

U.S. PATENT DOCUMENTS

| 7,214,667 B2 * | 5/2007 | Fukuda et al. ................. 514/62 |
| 2007/0116827 A1 | 5/2007 | Prakash et al. |
| 2007/0141181 A1 | 6/2007 | Henderson et al. |

FOREIGN PATENT DOCUMENTS

| EP | 1118332 A1 * | 7/2001 |
| EP | 1354590 A1 | 10/2003 |
| JP | 2007-161688 A | 6/2007 |
| WO | WO 03/002125 A2 * | 1/2003 |

OTHER PUBLICATIONS

The Merck Manual, 16th Ed., 1999, pp. 339-342 and 1488-1490.*
Parth Patwari, et al., "Mannosamine Inhibits Aggrecanase-Mediated Changes in the Physical Properties and Biochemical Composition of Articular Cartilage," Archives of Biochemistry and Biophysics, Feb. 1, 2000, pp. 79-85, vol. 374, No. 1.
International Search Report for International Application No. PCT/EP2008/067683, dated Feb. 18, 2009.
Spanish Search Report for Spanish Application No. 200703459, dated Aug. 7, 2009.

* cited by examiner

*Primary Examiner* — Shaojia Anna Jiang
*Assistant Examiner* — Ganapathy Krishnan
(74) *Attorney, Agent, or Firm* — Sughrue Mion, PLLC

(57) ABSTRACT

The present invention relates to compositions comprising chondroitin sulphate and mannosamine or a derivative thereof. The mannosamine derivative is preferably N-acetylmannosamine. The compositions may comprise glucosamine. Said compositions are useful in the treatment or prevention of degenerative joint diseases, preferably of osteoarthritis, in the treatment or prevention of tendon or ligament diseases, disorders or injuries and of immune system diseases, preferably of rheumatoid arthritis.

20 Claims, 2 Drawing Sheets

CS = chondroitin sulphate, sodium salt
Man = mannosamine hydrochloride

ANOVA; p<0.001
CS = chondroitin sulphate, sodium salt
Man = mannosamine hydrochloride
Glu = glucosamine hydrochloride Kruskal Wallis; p<0.001
CS = chondroitin sulphate, sodium salt
Man = mannosamine hydrochloride
Glu = glucosamine hydrochloride

COMPOSITION FOR THE TREATMENT OF OSTEOARTHRITIS

CROSS REFERENCE TO RELATED PATENT APPLICATION

This application is a National Stage of International Application No. PCT/EP2008/067683, filed on Dec. 17, 2008, which claims priority from Spanish Patent Application No. P200703459, filed Dec. 28, 2007, the contents of all of which are incorporated herein by reference in their entirety.

TECHNICAL FIELD OF THE INVENTION

The present invention relates to new compositions comprising chondroitin sulphate and an amino sugar. Likewise, the present invention relates to the use of the compositions in medicine.

BACKGROUND OF THE INVENTION

Osteoarthritis (arthrosis) is a degenerative joint disease which affects most people from 65 years of age, and which is characterized by a gradual degradation of cartilaginous tissue, combined with the presence of inflammation and pain. Synovial inflammation normally occurs later, when the disease is in an advanced state, and generally, it is only a secondary component in osteoarthritic pathology.

Osteoarthritis can be defined as the degeneration of hyaline articular cartilage. A secondary effect thereto is the damage of the synovial membrane and the subchondral bone (the bone in contact with the cartilage), as well as the formation of new bone at the margins of the surfaces of the joint.

Cartilage allows bones to move sliding over one another. It also absorbs the tension caused by the physical movement. In osteoarthritis, the cartilage surface breaks and wears away, causing the bones to move against one another, causing friction, pain, swelling and loss of movement in the joint. As time goes on the joint can be deformed.

In normal conditions, cartilage renewal is a very slow process consisting of a constant synthesis (anabolism) and degradation (catabolism) of the components of the extracellular matrix. The chondrocyte is the cell responsible for this metabolism, a process which must be perfectly coordinated.

Although the etiology of osteoarthritis is still not known, it is currently accepted as true that the first alterations occur at chondrocyte level, said alterations will subsequently give rise to the onset of an osteoarthritic joint.

A series of risk factors for the onset of the disease has been described, some of them include: aging, heredity, obesity, overload disorders, physical overtraining in sportsmen, injuries or traumas, work activity and low bone mineral density.

Osteoarthritis is a disease that does not have a definitive treatment. The following current therapeutic possibilities will be emphasized:

Fast acting symptomatic drugs. Among them are to be found: analgesics, nonsteroidal anti-inflammatory drugs (NSAIDs), corticoids and cyclooxygenase-2 (COX-2) selective inhibitors. The use of some of them involves a high risk of potentially serious side-effects, such as gastrointestinal problems in the case of NSAIDs.

Slow acting symptomatic drugs. They are known as SYSADOA (Symptomatic Slow Acting Drug for Osteoarthritis) (M. G. Lequesne, *Rev. Rhum.* (Eng./Ed.), 61, 69-73 (1994); B. F. Leeb et al., *J. Rheumatol.*, 27, 205-211 (2000)). Some of these substances include: hyaluronic acid, chondroitin sulphate and glucosamine hydrochloride. This group is characterized by having an overall efficacy similar to NSAIDs and, furthermore, as additional advantages, a higher safety and a more prolonged action over time, even for some months after the suspension of the treatment (carry over effect). Some clinical trials carried out with hyaluronic acid (M. Dougados *Semin. Arthritis. Rheum.*, 30(2 Suppl 1), 19-25 (2000)) and chondroitin sulphate (D. Uebelhart et al., *Osteoarthritis Cart.*, 12, 269-276 (2004)) have shown the possibility that both compounds, in addition to acting as SYSADOA, can affect the course of the osteoarthritic disease, slowing down or delaying the disease such as S/DMOAD (Structure/Disease Modifying anti-Osteoarthritis Drug) drugs.

Ligaments and tendons are periarticular structures having a limited self-repairing capacity, especially in adult persons.

The functional and structural properties of tendons and of ligaments are very similar. Tendons are anatomical structures attaching muscles to bones and ligaments are similar structures attaching bones to other bones. Both are cylindrical, elongated structures, formed from dense connective tissue and adapted to tension in one direction, with parallel collagen (mainly type I collagen) fibres. The reduced vascularisation of said tissues is one of the causes of the slow healing of tendons and ligaments.

The predominant cells in tendons are called tenocytes. The function of tenocytes is to maintain the matrix structure through degradation and synthesis processes. However, the tendon has a relatively low cell density and with little mitotic activity, which explains the reduced rate of replacement of this tissue and questions the degree in which these cells can promote intrinsic healing.

Damages in tendons and ligaments are caused by different factors, including injuries due to practicing sports or accidents, distensions, incorrect postures, bacterial infections, adverse drug reactions, arthritis in a joint, and as a result of different diseases.

The healing below the optimal level, the long rehabilitation period and a high incidence of relapse make it difficult to suitably treat tendon and ligament injuries.

The most frequent pharmacological treatments for tendinopathies (tendon diseases) and desmopathies (ligament diseases) include the following: rest, physical therapy (exercises, massages, ultrasound, laser, hydrotherapy, heat and cold), dietary supplements, surgery and medicaments, including nonsteroidal anti-inflammatory drugs (NSAIDs), glucocorticoids and antibiotics, the latter in the event that the disease has been caused by an infection. It is known that both NSAIDs and glucocorticoids have side-effects. Furthermore, recent publications question the efficacy of NSAIDs in tendon regeneration (D. Marsolais et al., "Nonsteroidal anti-inflammatory drug reduces neutrophil and macrophage accumulation but does not improve tendon regeneration", *Lab. Invest.* 83(7), 991-999 (2003)).

In the last few years, investigations are being conducted on the treatment of tendinopathies and desmopathies with stem cells, tenocytes, ligament cells, growth factors or with genes.

The immune system disease called rheumatoid arthritis is a chronic and progressive inflammatory disorder, characterized by the onset of synovitis and a severe joint destruction.

The pathogenesis of rheumatoid arthritis is a complex process, involving cell proliferation and fibrosis at the synovial membrane level, the formation of pannus and cartilage and bone erosion. This process is mediated by interdependent network of cytokines, prostanoids and proteolytic enzymes.

The intermediate objectives in the treatment of rheumatoid arthritis are: controlling inflammatory symptoms, reducing pain, preventing or controlling the joint damage and preventing the loss of function, and the ultimate purpose of the treatment is to induce the complete remission of the disease, although this occurs infrequently.

Chondroitin sulphate is a natural sulphated glycosaminoglycan with a polymeric structure characterized by a disaccharide which is repeated, formed by N-acetyl-D-galactosamine and D-glucuronic acid. Most of the N-acetyl-D-galactosamine residues are sulphated. Chondroitin sulphate is an essential component of the aggrecan which is located in articular cartilage.

The use of chondroitin sulphate for treating different diseases, for example in the treatment of cardiovascular diseases (U.S. Pat. No. 3,895,106) or in the treatment of psoriasis (WO2005/014012), has been described, however, its most extended use is in the treatment of osteoarthritis (M. G. Lequesne, *Rev. Rhum. Eng. Ed.*, 61, 69-73 (1994); G. Verbruggen et al., *Osteoarthritis Cart.*, 6 (Supplement A), 37-38 (1998)), generally by means of the administration of 800-1, 200 mg a day.

Contradictory results have been published on the use of chondroitin polysulphate in the treatment of tendinopathies. Although some authors describe its beneficial effect (H. Sundqvist et al., *Int. J. Sports Med.* 8, 298-303 (1987)), other authors, however, do not find significant differences between treated tendons and the control group (S. J. Dyson, *Equine Vet. J.* 36(5), 415-419 (2004)).

D-mannosamine (2-amino-2-deoxy-D-mannose) is an amino sugar the most extended use of which is in the synthesis of sialic acid and derivatives thereof, due to the fact that the physiological precursor of natural sialic acids is the N-acetylmannosamine. The use of N-acylmannosamines (N-acetyl, N-propanoyl, N-glycolyl, N-formylmannosamine) has also been described in the modulation of neuronal growth (WO 00/07602), and recently the use of N-acetylmannosamine for increasing the level of sexual hormones, particularly of testosterone (WO 2007/104576).

The amino sugar D-glucosamine (2-amino-2-deoxy-D-glucose) is an intermediate substrate used by articular cartilage in the synthesis of glycosaminoglycans and proteoglycans.

Several research groups have studied the effects of glucosamine hydrochloride in osteoarthritis (for example, H. Nakamura et al. *Clin. Exp. Rheumatol.* 22 (3), 293-9, (2004)).

There are documents in which compositions comprising chondroitin sulphate and amino sugars are described.

U.S. Pat. No. 5,587,363 describes a composition comprising chondroitin sulphate and glucosamine.

EP 1354590 claims an agent for treating articular disorders comprising an amino sugar and trehalose. The agent can comprise a glycosaminoglycan. Said document describes mixtures of chondroitin sulphate and glucosamine with and without trehalose, and also the combination of keratan sulphate, mannosamine and trehalose, as well as their activity in a type II collagen-induced arthritis model. The combination of chondroitin sulphate with mannosamine is neither described nor suggested in the document.

Due to the foregoing, the problem in which the present invention is based is that of providing an alternative treatment for osteoarthritis, periarticular diseases, in particular tendon or ligament diseases and immune system diseases, in particular rheumatoid arthritis.

DISCLOSURE OF THE INVENTION

The present invention relates to a composition comprising chondroitin sulphate and an amino sugar, wherein the amino sugar is selected from the group consisting of mannosamine and a mannosamine derivative, as well as mixtures thereof.

In a preferred embodiment of the invention, the amino sugar is mannosamine.

In another equally preferred embodiment, the amino sugar is a mannosamine derivative, preferably N-acetylmannosamine.

In another embodiment of the invention, the amino sugar is a combination of mannosamine and N-acetylmannosamine.

In another embodiment of the invention, the composition comprises glucosamine.

In another embodiment of the invention, the ratio by weight between chondroitin sulphate and the amino sugar is comprised between 1:0.1 and 1:2, the ratio by weight preferably varies between 1:0.1 and 1:0.7.

In a particular embodiment of the invention, the composition of the invention is a pharmaceutical composition. In a preferred embodiment, the pharmaceutical composition is for oral administration. In another preferred embodiment, the pharmaceutical composition is for intra-articular administration.

In another particular embodiment of the invention, the composition of the invention is a food composition. In another embodiment, the food composition is a functional food. In another embodiment, the food composition is a nutraceutical composition, also called food supplement. Functional foods can include dairy products, milk, yogurt, cereals, biscuits, fruit juices, vegetable juices, baby food and dehydrated food.

Other components, such as vitamins, can be added both to the food composition and to the pharmaceutical composition.

The present invention also relates to a process for preparing a previously defined composition comprising:
a) preparing an aqueous solution comprising chondroitin sulphate;
b) preparing an aqueous solution comprising the amino sugar; and
c) mixing the solutions of steps a) and b); or
a) mixing chondroitin sulphate and the amino sugar in solid state;
b) sieving and homogenizing the mixture.

According to another aspect of the invention, a previously defined composition is disclosed for its use as a medicament.

The present invention also relates to the use of a previously defined composition for the treatment, prevention or prophylaxis of a degenerative joint disease, preferably of osteoarthritis.

The present invention also relates to the use of a previously defined composition for the preparation of a medicament for the treatment, prevention or prophylaxis of inflammation or of pain. The inflammation and the pain are preferably associated to osteoarthritis.

In another particular embodiment of the invention, the medicament is a chondroprotective agent.

It is also possible to use a previously defined composition for the preparation of a medicament for the treatment, prevention or prophylaxis of a periarticular disease, disorder or injury. The periarticular disease, disorder or injury is preferably a tendon or ligament disease, disorder or injury, preferably selected from the group consisting of tendinosis, tendinitis (tendonitis), rheumatoid tendinitis, peritendinitis, tenosynovitis, paratenonitis, and any desmopathy. Likewise, the periarticular disease, disorder or injury can be the result of a trauma, an overuse or a pathological condition, an infectious, metabolic or endocrine disease, for example.

Likewise, the medicament comprising the composition of the invention can be used in the treatment of the inflammation and of the pain associated to a periarticular disease, disorder or injury.

The present invention also relates to the use of a previously defined composition for the preparation of a medicament for the treatment, prevention or prophylaxis of an immune system disease, selected from the group consisting of rheumatoid arthritis, lupus erythematosus, Graves' disease, Reiter's syndrome and Sjogren's syndrome. The most preferred immune system disease among them is rheumatoid arthritis.

The invention also relates to a previously defined composition for its use in the treatment, prevention or prophylaxis of a disease selected from degenerative joint disease and periarticular disease. The amino sugar is preferably selected from mannosamine and N-acetylmannosamine. Also, the degenerative joint disease is preferably osteoarthritis and the periarticular disease is a tendon or ligament disease. The ratio by weight between chondroitin sulphate and the amino sugar is preferably comprised between 1:0.1 and 1:2 and the composition can comprise glucosamine.

The present invention also relates to a previously defined composition for its use in the treatment, prevention or prophylaxis of an immune system disease, preferably of rheumatoid arthritis.

The medicament is preferably suitable for oral, intra-articular, intralesional, perilesional administration, or for administration in an implant. Furthermore in the event that the disease is a periarticular disease, the medicament can be suitable for topical administration to an exposed tendon or ligament.

When the present invention mentions intralesional administration, it refers to the direct administration in the actual injury.

When the present invention mentions perilesional administration, it refers to the administration around the injury.

The food compositions of the present invention act by nourishing the cartilage, protecting the joints, improving the articular functional capacity, elasticity and flexibility and also have an effect of prevention and reversion of the physical overtraining syndrome in sportsmen, and of the undesirable effects associated thereto.

Chondroitin sulphate, a component of the compositions of the present invention, is a sulphated glycosaminoglycan with a molecular weight comprised between 10,000 daltons and 60,000 daltons, depending on the origin and process for obtaining it. It can be obtained from animal cartilaginous tissues, such as porcine or bovine cattle tracheas, and shark cartilaginous skeleton, according to processes described in the literature (ES 547769).

Its polymeric structure is characterized by a disaccharide which is repeated, formed by N-acetyl-D-galactosamine and D-glucuronic acid. Most of the N-acetyl-D-galactosamine residues are sulphated.

Chondroitin sulphate from cartilaginous issue is mainly found in two isomeric forms differing in the position of the sulphate group present in the N-acetylgalactosamine residue, chondroitin 4-sulphate (chondroitin sulphate A) and chondroitin 6-sulphate (chondroitin sulphate C), which are represented by the following structure:

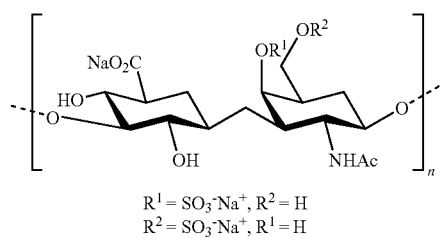

$R^1 = SO_3^- Na^+, R^2 = H$
$R^2 = SO_3^- Na^+, R^1 = H$

In addition to chondroitin 4-sulphate and chondroitin 6-sulphate, the term chondroitin sulphate also includes the following compounds:
chondroitin sulphate B, also known as dermatan sulphate;
chondroitin sulphate D, known as chondroitin 2,6-disulphate;
chondroitin sulphate E, known as chondroitin 4,6-disulphate.

In the present invention, the term "chondroitin sulphate" covers all these compounds, as well as mixtures thereof.

In chondroitin sulphate, the sulphate group is covalently bound to the sugar.

Due to the negative charges present in the molecule, chondroitin sulphate is in the form of salt, for example in commercial preparations chondroitin sulphate is in the form of sodium salt. Therefore, the term "chondroitin sulphate" includes the organic and inorganic salts thereof. Examples of organic salts include, for example, ethanolamine salts, triethanolamine salts and salts with basic amino acids. Examples of inorganic salts include, for example, sodium, potassium, calcium, magnesium, ammonium, lithium and aluminium salts. Said salts are generally prepared, for example, by reacting chondroitin sulphate in the form of free base with a stoichiometric amount of the suitable acid in water or in an organic solvent or in a mixture of both.

D-mannosamine (2-amino-2-deoxy-D-mannose) is an amino sugar with the following structure:

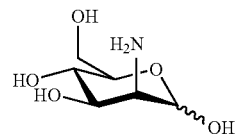

In the present invention, the term "mannosamine" includes mannosamine salts.

The amino sugars mannosamine, mannosamine derivatives, such as N-acetylmannosamine, glucosamine and salts thereof used in the present invention are preferably of the D series.

Said amino sugars can exist in α and β anomeric forms. The present invention includes the use of both the individual α and β anomers separated and the mixtures thereof.

Mannosamine salts with pharmaceutically acceptable acids, include, without limitation, the salts with the following acids: hydrochloric, hydroiodic, hydrobromic, phosphoric, sulphuric, methanesulfonic, acetic, formic, tartaric, maleic, citric, succinic, lactic, gluconic, pyruvic, fumaric, propionic, aspartic, glutamic, benzoic, ascorbic, glucuronic and malic acid.

Mannosamine salts can be prepared according to standard processes for the preparation of salts of amino sugars.

Said salts are generally prepared, for example, by reacting the base mannosamine, obtained from mannosamine hydrochloride, with a stoichiometric amount of the suitable acid.

Mannosamine hydrochloride is a commercial product (NZP, New Zealand Pharmaceutical), but if desired it can be prepared by means of the epimerization of N-acetylglucosamine with an aqueous Ca(OH)$_2$ solution followed by the separation of the isomers, treatment with hydrochloric acid, decolouration and precipitation or crystallization with solvents (Sugai et al., *Bull. Chem. Soc. Jpn.*, 68, 3581-3589 (1995); Sugai et al., *Tetrahedron*, 53 (7), 2397-2400 (1997)).

N-acetylmannosamine is a commercial product (NZP, New Zealand Pharmaceutical) but if desired it can be prepared by means of acetylation from mannosamine hydrochloride. Another N-acylmannosamine that can be used is N-propanoyl-D-mannosamine, for example.

In the present invention, the term "glucosamine" includes glucosamine salts.

Glucosamine salts with pharmaceutically acceptable acids include, without limitation, salts with the following acids: hydrochloric, hydroiodic, hydrobromic, phosphoric, sulphuric and methanesulfonic acid.

For the use in the treatment, prevention or prophylaxis of a degenerative joint disease, of inflammation, of pain, of a periarticular disease, disorder or injury, or of an immune system disease, the compositions of the invention are formulated in suitable pharmaceutical compositions, resorting to conventional techniques and excipients or carriers, such as those described in *Remington: The Science and Practice of Pharmacy* 2000, edited by Lippincott Williams and Wilkins, 20th edition, Philadelphia.

The nature of the pharmaceutical formulation will depend, as is well known, on the route of administration and on the nature of the pathology to be treated.

The pharmaceutical compositions of the invention can be administered to the patient in required doses. The administration of the compositions can be carried out by different routes, for example, oral, intravenous, intraperitoneal, intraarticular, intralesional, perilesional, intratendinous, peritendinous, intrathecal, subcutaneous, intramuscular, topical, sublingual, intradermal or intranasal route. The pharmaceutical compositions of the invention include a therapeutically effective amount of the active composition of the invention, said amount depending on many factors, such as for example the physical condition of the patient, age, sex, route of administration, severity of the symptoms and on other factors that are well known in the art. Furthermore, it will be understood that said dosage of active composition can be administered in single or multiple dose units to provide the desired therapeutic effects.

The pharmaceutical preparations of the invention will generally be in solid form, liquid form or as a gel. The pharmaceutical preparations in solid form that can be prepared according to the present invention include powders, pellets, microspheres, nanoparticles, tablets, dispersible granules, capsules, seals and suppositories. The preparations in liquid form include solutions, suspensions, emulsions, syrups and elixirs comprising commonly used inert diluents, such as distilled water, ethanol, sorbitol, glycerol or propylene glycols. The preparations in solid form which are to be converted, immediately before being used, into preparations in liquid form are also contemplated. Said liquid forms include solutions, suspensions and emulsions.

To prepare the food compositions (functional foods or nutraceutical compositions), the compositions of the invention are formulated with suitable components and/or excipients used in nutrition. The prepared food compositions can be, for example, in solid form, in liquid form, as an emulsion, as a suspension or as a gel. The preparations in solid form that can be converted, before being used, into preparations in liquid form or into suspensions are also contemplated.

According to the present invention, it has been found that the compositions of the invention have advantages, such as: (i) the composition of the invention comprising chondroitin sulphate and mannosamine hydrochloride is more effective than each of the components separately; (ii) there is a synergic effect between chondroitin sulphate and mannosamine hydrochloride when they are administered together; (iii) the composition of the invention, made of a mixture of chondroitin sulphate and mannosamine hydrochloride is significantly more effective than the composition made of a mixture of chondroitin sulphate and glucosamine hydrochloride (superior effect on proteoglycan synthesis); (iv) the composition of the invention containing chondroitin sulphate and mannosamine hydrochloride induced a dose dependent reduction of apoptosis of chondrocytes cultured with TNFα.

DETAILED DESCRIPTION OF THE PREFERRED EMBODIMENTS

Figure 1:
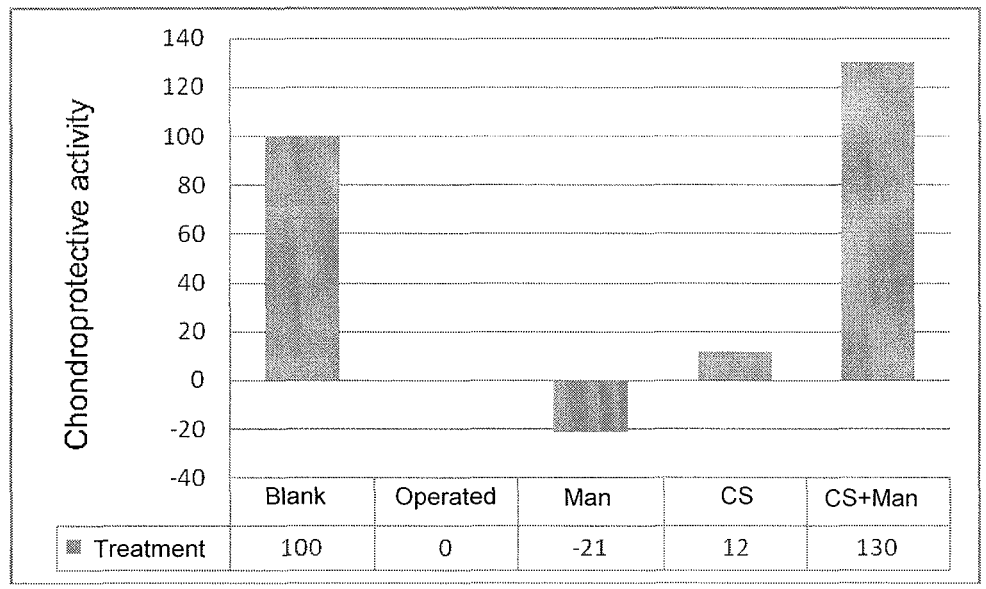
FIG. 1 shows the chondroprotective activity of a blank control group, an operated control group, an operated group treated with chondroitin sulphate, an operated group treated with mannosamine hydrochloride and an operated group treated with the composition formed by a mixture of chondroitin sulphate and mannosamine hydrochloride.

The following examples illustrate, but do not limit, the scope of the present invention.

Some examples of representative formulations for tablets and injectable preparations are mentioned below.

EXAMPLE 1

Chondroitin Sulphate and Mannosamine or N-Acetylmannosamine Tablets

The tablets were prepared according to conventional processes.

Content of active ingredients per tablet:

| | |
|---|---|
| Chondroitin sulphate, sodium salt | 400.0 mg |
| Mannosamine hydrochloride or N-acetylmannosamine | 400.0 mg |

EXAMPLE 2

Chondroitin Sulphate, Mannosamine and N-Acetylmannosamine Tablets

The tablets were prepared according to conventional processes.

Content of active ingredients per tablet:

| | |
|---|---|
| Chondroitin sulphate, sodium salt | 400.0 mg |
| Mannosamine hydrochloride | 200.0 mg |
| N-acetylmannosamine | 200.0 mg |

EXAMPLE 3

Chondroitin Sulphate, Mannosamine and Glucosamine Tablets

The tablets were prepared according to conventional processes.
Content of active ingredients per tablet:

| | |
|---|---|
| Chondroitin sulphate, sodium salt | 400.0 mg |
| Mannosamine hydrochloride | 200.0 mg |
| Glucosamine hydrochloride | 200.0 mg |

EXAMPLE 4

Chondroitin Sulphate and Mannosamine or N-Acetylmannosamine Injectable 2 mL of injectable formulation were prepared according to conventional processes.
Content of active ingredients per mL:

| | |
|---|---|
| Chondroitin sulphate, sodium salt | 75 mg/mL |
| Mannosamine hydrochloride or N-acetylmannosamine | 75 mg/mL |

Some examples of assays that can be used to determine the activity of the compositions of the present invention are mentioned below.

EXAMPLE 5

Evaluation of the In Vivo Chondroprotective Activity of the Combination of Chondroitin Sulphate and Mannosamine Hydrochloride The objective was to evaluate the chondroprotective activity (cartilage protective activity) of a composition formed by a mixture of chondroitin sulphate and mannosamine hydrochloride as sole active components, in a model of experimental osteoarthritis induced by partial medial meniscectomy in guinea pigs (A. M. Bendele, *Progressive chronic osteoarthritis in femorotibial joints of partial medial meniscectomized guinea pigs, Vet. Pathol.* 24, 444-448 (1987)), comparing said activity with the chondroprotective activity of chondroitin sulphate and of mannosamine hydrochloride.

Materials and Methods

Dunkin Hartley (DH) guinea pigs with a weight comprised between 580 and 699 g were used. A partial medial meniscectomy was performed in a part of them.

The following treatment groups were formed: blank control group (corresponding to healthy guinea pigs), operated control group (corresponding to guinea pigs in which a partial medial meniscectomy was performed to induce an experimental osteoarthritis in them), operated guinea pigs to which the sodium salt of chondroitin sulphate (95 mg/kg of body weight/day) was administered, operated guinea pigs to which mannosamine hydrochloride (60 mg/kg of body weight/day) was administered, operated guinea pigs to which a mixture of sodium salt of chondroitin sulphate (95 mg/kg of body weight/day) and mannosamine hydrochloride (60 mg/kg of body weight/day) was administered.

On the day after the surgery, the daily administration of the corresponding oral treatments by means of gastric gavage was started, the carrier used being water for injection. The blank control and operated control groups only received the carrier (water for injection) by oral route.

The treatments were administered once a day for 70 days (ten weeks). The body weight and the clinical signs of the animals were recorded twice a day. No remarkable clinical signs were observed throughout the treatment period.

On the day after the administration had ended, the animals were sacrificed by anaesthetic overdose (pentobarbital sodium) and the femorotibial joint of the right rear leg was removed for its fixing in 10% formol for at least 48 hours. Then, they were decalcified, included in paraffin, the necessary sections were obtained and the stainings with Hematoxylin-Eosin and Safranin-O-Fast Green (or Toluidine Blue) were performed for their histological evaluation, which was performed by a pathologist in a blind manner.

The severity of the osteoarthritic injuries was evaluated by means of the modified histologic/histochemical scale of Mankin et al. (H J. Mankin and L. Lipiello *Biochemical and metabolic abnormalities in articular cartilage from osteoarthritic human hips. J. Bone Joint Surg.-Amer.* 53-A, 523-537 (1971)).

The scale evaluates the severity of the osteoarthritic injuries based on the loss of glycosaminoglycan (GAG) content, structure changes and cell changes. A total global histopathological score can be obtained by means of the Mankin scoring system, which for each animal is the sum of several parameters: loss of GAGs, cartilage structure, loss of chondrocytes, formation of clones and line integrity.

The evaluation of the amount of glycosaminoglycans (GAGs) was performed by means of 2 stainings: Toluidine Blue and Safranin O-Fast Green. The loss of red colour intensity with Safranin (or blue colour with Toluidine Blue) indicates a loss of proteoglycans, which is observed with the degenerative changes of the cartilage.

The Hematoxylin-Eosin staining is used to evaluate the changes in the structure of the cartilage and changes at cell level.

Two types of evaluations of the obtained data were performed:

Chondroprotective Activity

Based on the results obtained with the Toluidine Blue and Hematoxylin-Eosin staining, the calculation of the chondroprotective activity was carried out.

For the calculation of the chondroprotective activity, first the index of incidence of each parameter ($I_{parameter}$) was obtained by multiplying the value of the described score ($S_i$) by the number of animals having such score ($n_i$). Since the sizes of each group are not identical, they were standardized dividing by the total number of individuals of the group and multiplying by 100:

$$I_{parameter} = \frac{\Sigma(n_i \times S_i)}{\Sigma n_i} \times 100$$

Then, the chondroprotective activity of each treatment was calculated as the coefficient of variation from the index obtained in each of the three parameters (GAGs, cartilage structure, chondrocyte proliferation) according to the following formula:

$$\text{Chondroprotective activity} = CV = \frac{I_{Operated\ control} - I_{Treatment}}{I_{Operated\ control} - I_{Blank\ control}} \times 100$$

Taking 100% as a reference for the blank control group and 0% for the operated control group, the average chondroprotective activity of the three parameters was represented.

Results

As can be seen in FIG. 1, it can be considered that there are neither differences between the group treated with chondroitin sulphate (12%) and the operated group (0%), nor between the group treated with mannosamine hydrochloride (−21%) and the operated group (0%) either. However, when the mixture of chondroitin sulphate and mannosamine hydrochloride was administered to a group of operated guinea pigs, there was a synergic increase of the chondroprotective activity, a value (130%), similar to the blank control group (100%) being reached.

Evaluation by the Modified Mankin Method

With the scoring system, separate scores were assigned for the Safranin staining of GAGs (score of 0-6), loss of chondrocytes (score of 0-4), structure (score of 0-8), formation of clones (score of 0-3) and line integrity (score of 0-1). Then, the scores obtained in each subcategory for each animal were added and the global histopathological score was obtained. The statistical evaluation between the different groups was carried out by means of the Mann-Whitney U test (F. J. Gravetter and L. B. Wallnau, *Statistics for the Behavioral Sciences*, Wadsworth Publishing, 7 edition, 2006) (see Table 1).

TABLE 1

|  | Man 60 mg/kg/day | CS 95 mg/kg/day | CS 95 + Man 60 mg/kg/day |
| --- | --- | --- | --- |
| Operated control | 1.000 | 0.577 | 0.049* |

*p < 0.05. Mann-Whitney test
CS = chondroitin sulphate, sodium salt
Man = mannosamine hydrochloride Results In the experimental conditions of the following study, and as it can be observed in Table 1, it is confirmed that there are no statistically significant differences between the operated group and the group treated with mannosamine hydrochloride. The group treated with chondroitin sulphate caused an improvement with respect to the operated group, but without statistical significance. In the group treated with the chondroitin sulphate and mannosamine hydrochloride combination, statistically significant improvements were achieved with respect to the operated group (p<0.05).

Conclusions

The treatment with the combination of chondroitin sulphate and mannosamine hydrochloride led to a lower incidence of injuries together with the blank control group (healthy guinea pigs).

There is a synergic effect between mannosamine hydrochloride and chondroitin sulphate when they are administered together. Mannosamine hydrochloride causes a synergic increase of the action of chondroitin sulphate.

EXAMPLE 6

Determination of Proteoglycan Synthesis.
Comparative Study of the Chondroitin Sulphate and Mannosamine Hydrochloride Combination Versus Chondroitin Sulphate and Glucosamine Hydrochloride Combination The objective was to observe the effect of a composition of the invention, made of a mixture of chondroitin sulphate and mannosamine hydrochloride (CS+Man), and of a composition made of a mixture of chondroitin sulphate and glucosamine hydrochloride (CS+Glu), on proteoglycan synthesis.

Materials and Methods

Solutions were prepared with the two compositions. The composition of the invention (CS+Man) contained 0.27 mg of sodium salt of chondroitin sulphate and 0.17 mg of mannosamine hydrochloride, and the composition (CS+Glu) contained 0.27 mg of sodium salt of chondroitin sulphate and 0.17 mg of glucosamine hydrochloride. Each composition was dissolved in 1 mL of culture medium.

Bovine chondrocytes were cultured for 10 days in alginate beads (as described by B. Beekman et al., *Exp. Cell Res.* 237, 135-141 (1997); *Biochem. Biophys. Res. Comm.* 237, 107-110 (1997); *Osteoarthritis and Cartilage* 6, 330-340 (1998)); at 5 beads per well; 250 µL of culture medium per well; 48-well plates, in the absence (control) or presence of the composition. Twice weekly, medium is refreshed. After 10 days, the beads are harvested (5 beads in each culture well, n=3 wells per treatment, n=8 wells for control), and stored at −20° C. until analyses.

Synthesis of proteoglycans were determined as glycosaminoglycan (GAG) levels (µg of GAGs per bead).

Results

Figure 2:
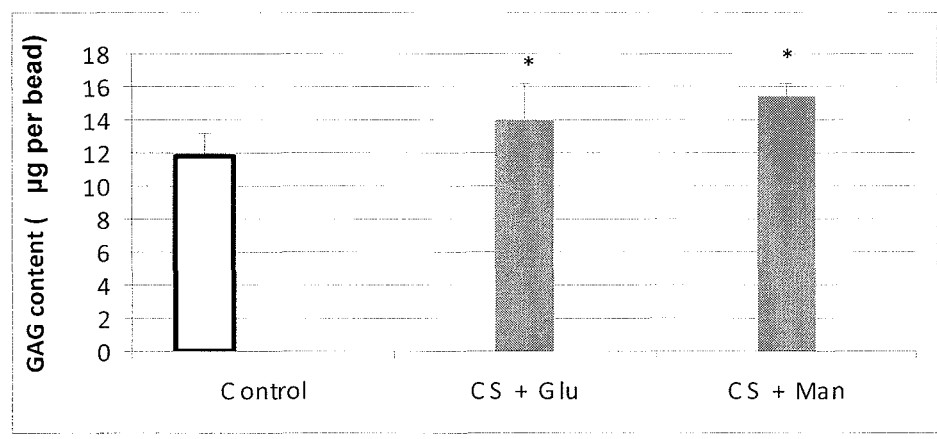
FIG. 2 shows the effect of the composition of the invention formed by a mixture of chondroitin sulphate and mannosamine hydrochloride and the composition formed by a mixture of chondroitin sulphate and glucosamine hydrochloride on the synthesis of proteoglycans, determined as GAG content.

As can be seen in FIG. 2, a significant stimulatory effect of proteoglycan synthesis was found in the mixtures CS+Glu and CS+Man compared to the control. However, the composition of the invention formed by a mixture of chondroitin sulphate and mannosamine hydrochloride showed a superior effect than the composition formed by a mixture of chondroitin sulphate and glucosamine hydrochloride.

EXAMPLE 7

Determination of Chondrocyte Apoptosis.
Comparative Study of the Chondroitin Sulphate and Mannosamine Hydrochloride Combination Versus Chondroitin Sulphate and Glucosamine Hydrochloride Combination The objective was to observe the effect of a composition of the invention, made of a mixture of chondroitin sulphate and mannosamine hydrochloride (CS+Man), and of a composition made of a mixture of chondroitin sulphate and glucosamine hydrochloride (CS+Glu), on chondrocyte apoptosis.

Materials and Methods

Bovine chondrocytes were cultured for 48 hours in alginate beads (as described by B. Beekman et al., *Exp. Cell Res.* 237, 135-141 (1997); *Biochem. Biophys. Res. Comm.* 237, 107-110 (1997); *Osteoarthritis and Cartilage* 6, 330-340 (1998)); at 5 beads per well; 250 µL of culture medium per well; 48-well plates, with TNFa (tumor necrosis factor-alpha) and the absence (control) or presence of the composition. Then, the beads were harvested (3 wells per treatment, 8 wells for control), and stored at −20° C. until analyses.

Each composition was tested at the following concentrations:

Composition of invention CS+Man:

High concentration: 1.07 mg of sodium salt of chondroitin sulphate+0.67 mg of mannosamine hydrochloride, dissolved in 1 ml of culture medium.

Low concentration: 0.54 mg of sodium salt of chondroitin sulphate+0.34 mg of mannosamine hydrochloride, dissolved in 1 ml of culture medium.

Composition CS+Glu:

High concentration: 1.07 mg of sodium salt of chondroitin sulphate+0.67 mg of glucosamine hydrochloride, dissolved in 1 ml of culture medium.

Low concentration: 0.54 mg of sodium salt of chondroitin sulphate+0.34 mg of glucosamine hydrochloride, dissolved in 1 ml of culture medium.

Apoptosis of chondrocytes was measured using a kit based on the fluorogenic detection of caspase-3 and caspase-7 activity following cell lysis.

Results

Figure 3:
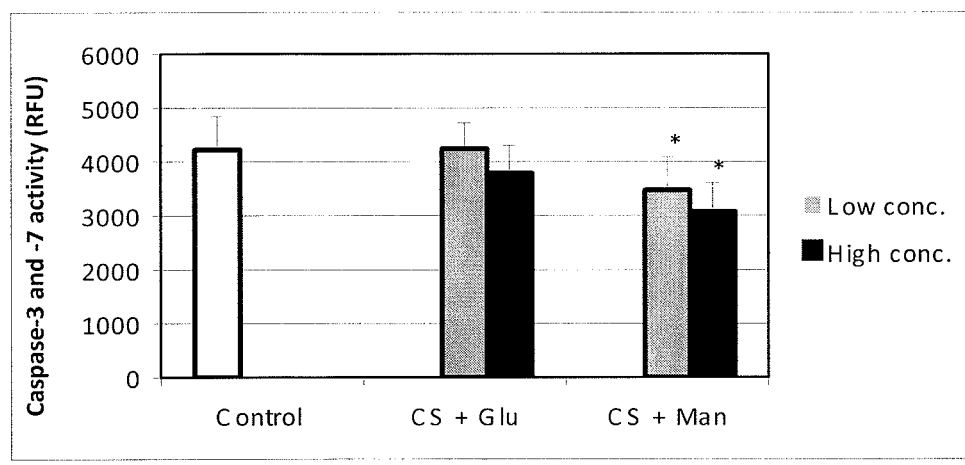
FIG. 3 shows the effect of the composition of the invention formed by a mixture of chondroitin sulphate and mannosamine hydrochloride and the composition formed by a mixture of chondroitin sulphate and glucosamine hydrochloride on apoptosis of chondrocytes, measured as Caspase-3/7 activity and reported as RFU (relative fluorescence units).

As can be seen in FIG. 3, the composition of invention formed by a mixture of chondroitin sulphate and mannosamine hydrochloride induced a dose dependent, statistically significant reduction of apoptosis of chondrocytes cultured with TNF$\alpha$ at all the doses. In contrast, the composition formed by a mixture of chondroitin sulphate and glucosamine hydrochloride did not show a statistically significant effect.

The invention claimed is:

1. A composition comprising chondroitin sulphate and an amino sugar, wherein the amino sugar is at least one selected from the group consisting of mannosamine and N-acetylmannosamine, and wherein the ratio by weight of chondroitin sulphate to amino sugar is between 1:0.1 and 1:2.

2. The composition according to claim 1, wherein the amino sugar is mannosamine.

3. The composition according to claim 1, wherein the amino sugar is N-acetylmannosamine.

4. The composition according to claim 1, wherein the amino sugar is a combination of mannosamine and N-acetylmannosamine.

5. The composition according to claim 2, further comprising glucosamine.

6. A medicament comprising the composition according to claim 1, and at least one pharmaceutically acceptable excipient.

7. The medicament according to claim 6, wherein the medicament is for oral administration.

8. The medicament according to claim 6, wherein the medicament is for intra-articular administration.

9. A food composition comprising the composition according to claim 1.

10. The food composition according to claim 9, wherein the food composition is a functional food.

11. The food composition according to claim 9, wherein the food composition is a nutraceutical composition.

12. A process for preparing a composition according to claim 1, comprising (A) or (B):
 wherein (A) comprises:
  i) preparing an aqueous solution comprising chondroitin sulphate;
  ii) preparing an aqueous solution comprising the amino sugar; and
  iii) mixing the solutions of steps i) and ii);
 wherein (B) comprises:
  mixing chondroitin sulphate and the amino sugar in solid state; and
  sieving and homogenizing the mixture.

13. A method for treating a degenerative joint disease comprising administering to a patient a therapeutically effective amount of the medicament according to claim 6.

14. The method according to claim 13, wherein the degenerative joint disease is osteoarthritis.

15. A method for treating inflammation or pain comprising administering to a patient a therapeutically effective amount of the medicament according to claim 6.

16. The method according to claim 15, wherein the inflammation or the pain are associated to osteoarthritis.

17. The method according to claim 13, wherein the medicament is a chondroprotective agent.

18. A method for treating rheumatoid arthritis comprising administering to a patient a therapeutically effective amount of the medicament according to claim 6.

19. A method for nourishing the cartilage, protecting the joints, improving the articular functional capacity or improving the articular elasticity comprising administering to a mammal in need thereof the food composition according to claim 9.

20. A method for nourishing the cartilage, protecting the joints, improving the articular functional capacity or improving the articular elasticity comprising administering to a mammal in need thereof the functional food according to claim 10 or the nutraceutical composition according to claim 11.

* * * * *

UNITED STATES PATENT AND TRADEMARK OFFICE
CERTIFICATE OF CORRECTION

PATENT NO. : 8,445,462 B2
APPLICATION NO. : 12/810775
DATED : May 21, 2013
INVENTOR(S) : Josep Escaich Ferrer et al.

It is certified that error appears in the above-identified patent and that said Letters Patent is hereby corrected as shown below:

In the Claims:

Col. 13, line 29, Claim 1, line 1: A composition comprising chondroitin sulphate and an Delete "comprising"

Insert --consisting essentially of--

Col. 13, line 33, Claim 1, line 5: sulphate to amino acid sugar is between 1:0.1 and 1:2.

Delete "1:2"

Insert --1:0.7--

Signed and Sealed this
Third Day of September, 2013

Teresa Stanek Rea
*Acting Director of the United States Patent and Trademark Office*